United States Patent
Brigham et al.

(10) Patent No.: US 11,553,847 B2
(45) Date of Patent: Jan. 17, 2023

(54) PULSE WAVE DETECTING DEVICE

(71) Applicant: OMRON HEALTHCARE Co., Ltd., Kyoto (JP)

(72) Inventors: Brian Brigham, Kyoto (JP); Masayuki Fukutsuka, Kyoto (JP); Shingo Yamashita, Kyoto (JP); Tsuyoshi Kitagawa, Kyoto (JP); Toshihiko Ogura, Kyoto (JP); Masayuki Wakamiya, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 336 days.

(21) Appl. No.: 15/914,825

(22) Filed: Mar. 7, 2018

(65) Prior Publication Data
US 2018/0192892 A1    Jul. 12, 2018

Related U.S. Application Data

(63) Continuation of application No. PCT/JP2016/073852, filed on Aug. 15, 2016.

(30) Foreign Application Priority Data

Sep. 7, 2015 (JP) .............................. JP2015-175964

(51) Int. Cl.
*A61B 5/022* (2006.01)
*A61B 5/00* (2006.01)

(52) U.S. Cl.
CPC ............ *A61B 5/022* (2013.01); *A61B 5/6824* (2013.01); *A61B 5/6843* (2013.01)

(58) Field of Classification Search
None
See application file for complete search history.

(56) References Cited

U.S. PATENT DOCUMENTS 5,467,771 A    11/1995   Narimatsu et al.
6,210,340 B1    4/2001   Amano et al.
(Continued)

FOREIGN PATENT DOCUMENTS

CN           1524490 A        9/2004
JP          H01-122704 U      8/1989
(Continued)

OTHER PUBLICATIONS

"Hole." Hole | Definition in the Cambridge English Dictionary, Cambridge Dictionary, Aug. 18, 2015, dictionary.cambridge.org/us/dictionary/english/hole (Year: 2015).*
English Translation of WO-2008087870 (Year: 2008).*
International Search Report issued in Application No. PCT/JP2016/073852, dated Oct. 25, 2016 (6 pages).
Written Opinion issued in Application No. PCT/JP2016/073852, dated Oct. 25, 2016 (4 pages).
International Preliminary Report on Patentability issued in Application No. PCT/JP2016/073852, dated Jul. 13, 2017 (7 pages).
(Continued)

*Primary Examiner* — Jacqueline Cheng
*Assistant Examiner* — Jairo H Portillo
(74) *Attorney, Agent, or Firm* — Osha Bergman Watanabe & Burton LLP

(57) ABSTRACT

A pulse wave detecting device includes: a pressure pulse wave detector which is configured to press a pressing surface in which a pressure detecting element is formed, against a radial artery under a skin of a wrist of a subject, and which is configured to detect a pressure pulse wave from the radial artery; and a housing which accommodates the pressure pulse wave detector in a state where the pressing surface is exposed toward the wrist. The housing is configured so that a compression pressure which is exerted by the housing in an attachment state where the housing is attached to the wrist, and which is applied onto the radial artery is smaller than a compression pressure which is exerted by the pressing surface in the attachment state, and which is applied onto the radial artery.

2 Claims, 8 Drawing Sheets

(56) References Cited

U.S. PATENT DOCUMENTS

| | | | | |
|---|---|---|---|---|
| 6,312,393 | B1* | 11/2001 | Abreu | A61B 3/1241 |
| | | | | 600/558 |
| 2002/0188209 | A1* | 12/2002 | Ogura | A61B 5/02028 |
| | | | | 600/490 |
| 2003/0149369 | A1 | 8/2003 | Gallant et al. | |
| 2006/0111636 | A1* | 5/2006 | Jacober | A61B 5/021 |
| | | | | 600/490 |
| 2011/0009757 | A1* | 1/2011 | Sano | A61B 5/02233 |
| | | | | 600/499 |
| 2012/0221041 | A1* | 8/2012 | Hansson | A61B 17/135 |
| | | | | 606/203 |
| 2013/0190576 | A1* | 7/2013 | Matsumura | A61B 5/022 |
| | | | | 600/301 |
| 2015/0018869 | A1* | 1/2015 | Benz | A61B 17/135 |
| | | | | 606/203 |
| 2015/0265214 | A1* | 9/2015 | De Kok | A61B 5/681 |
| | | | | 600/301 |
| 2015/0346766 | A1* | 12/2015 | Justice | H01M 10/425 |
| | | | | 429/100 |

FOREIGN PATENT DOCUMENTS

| | | | |
|---|---|---|---|
| JP | H03-114207 | U | 11/1991 |
| JP | H05-329117 | A | 12/1993 |
| JP | 2002-224064 | A | 8/2002 |
| JP | 2008-168054 | A | 7/2008 |
| JP | 5329117 | B2 | 10/2013 |
| WO | 98/042254 | A1 | 10/1998 |
| WO | WO-2008087870 | A1 * 7/2008 | ............... A61B 5/02 |

OTHER PUBLICATIONS

Extended European Search Report issued in European Application No. 16844124.4, dated Feb. 26, 2019 (7 pages).

Office Action issued in Chinese Applicaese tion No. 201680051626.2, dated Mar. 11, 2020 (13 pages).

* cited by examiner

PULSE WAVE DETECTING DEVICE

CROSS-REFERENCE TO RELATED APPLICATION(S)

This application is a continuation of PCT application No. PCT/JP2016/073852, which was filed on Aug. 15, 2016 based on Japanese Patent Application (No. 2015-175964) filed on Sep. 7, 2015, the contents of which are incorporated herein by reference.

BACKGROUND

1. Technical Field

The present invention relates to a pulse wave detecting device.

2. Background Art

A biological information measuring device of the wrist wearing type is known that, in a state where a pressure detecting element is pressed against a living body portion through which an artery such as the radial artery in the wrist passes, can measure biological information such as the pulse and the blood pressure by using information detected by the pressure detecting element (for example, see JP-A-2008-168054 and JP-A-05-329117).

In the biological information measuring device disclosed in JP-A-2008-168054, in the case where the radial artery is compressed by the pressure detecting element, the radial artery is compressed also by a housing in which the pressure detecting element is mounted. When the compression pressure which is exerted by the housing, and which is applied onto the wrist is larger than that which is exerted by the pressure detecting element, which is applied onto the wrist, it is impossible to accurately detect a pressure pulse wave.

The biological information measuring device disclosed in JP-A-05-329117 is configured so that a restriction wall disposed around the pressure detecting element enables the pressure detecting element to be projected toward the wrist by an adequate distance. Therefore, the wrist is compressed also by the restriction wall. When the compression pressure which is exerted by the restriction wall, and which is applied onto the wrist is larger than that which is exerted by the pressure detecting element, and which is applied onto the wrist, it is impossible to accurately detect a pressure pulse wave.

In JP-A-2008-168054 and JP-A-05-329117, the problem that the accuracy of detection of a pressure pulse wave is lowered is not considered.

SUMMARY

The invention has been conducted in view of the above circumstances. It is an object of the invention to provide a pulse wave detecting device in which the accuracy of detection of a pressure pulse wave can be improved.

According to an aspect of the invention, there is provided a pulse wave detecting device including: a pressure pulse wave detector which is configured to press a pressing surface in which a pressure detecting element is formed, against a skin above a radial artery in a wrist of a subject, and which is configured to detect a pressure pulse wave from the radial artery; and a housing which accommodates the pressure pulse wave detector in an attachment state where the pressing surface is exposed toward the wrist, wherein, in an attachment state where the housing is attached to the wrist, a portion of the housing which, at a position adjacent to the pressing surface, is contacted with the skin above the radial artery together with the pressing surface, is deformable in a direction perpendicular to the pressing surface, and a compression pressure which is exerted by the portion of the housing in the attachment state, and which is applied onto the radial artery is smaller than a compression pressure which is exerted by the pressing surface, and which is applied onto the radial artery.

DESCRIPTION OF EXEMPLARY EMBODIMENTS

Hereinafter, an embodiment of the invention will be described with reference to the drawings.

Figure 1:
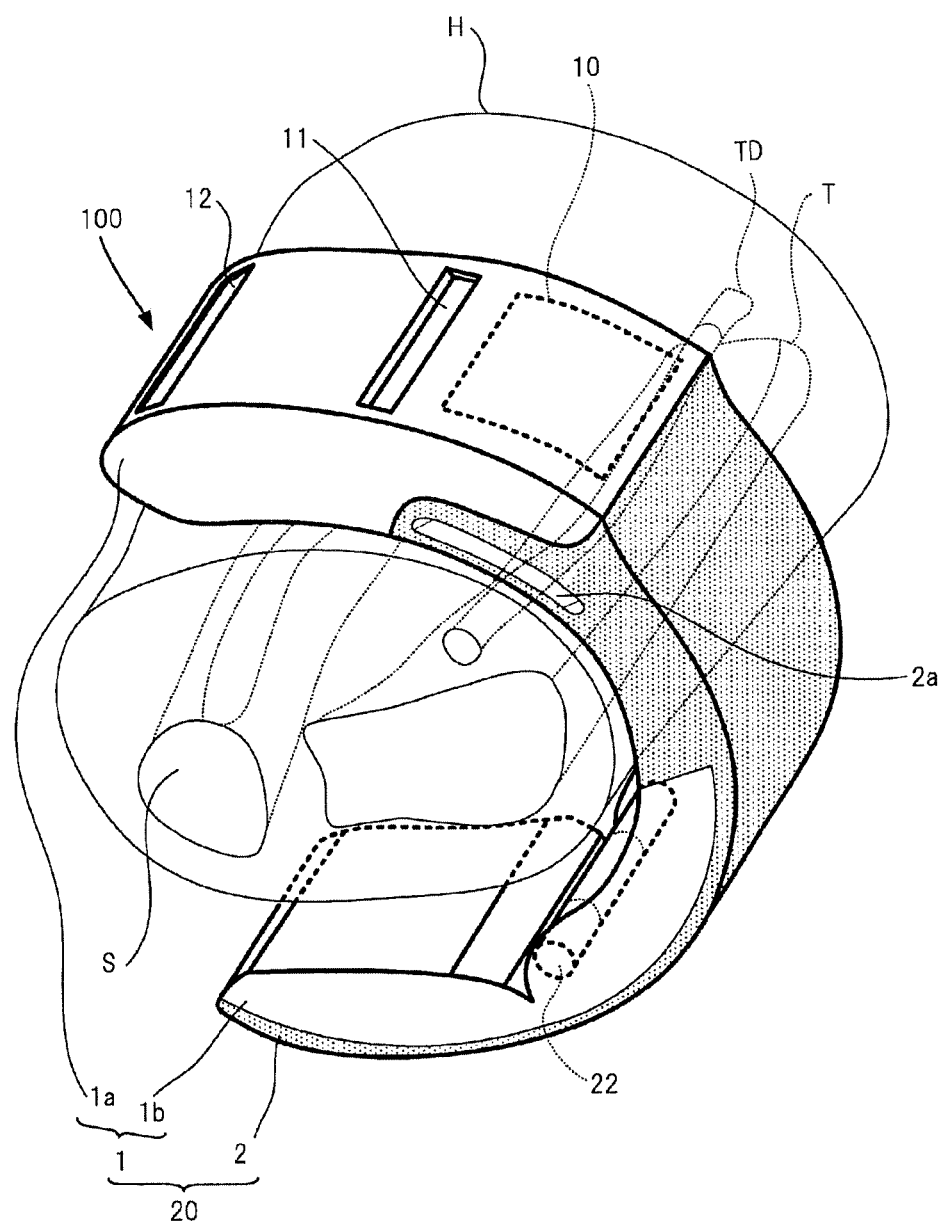
FIG. 1 is a diagram showing the external configuration of a housing 20 of a biological information measuring device for illustrating an embodiment of the invention.
Figure 2:
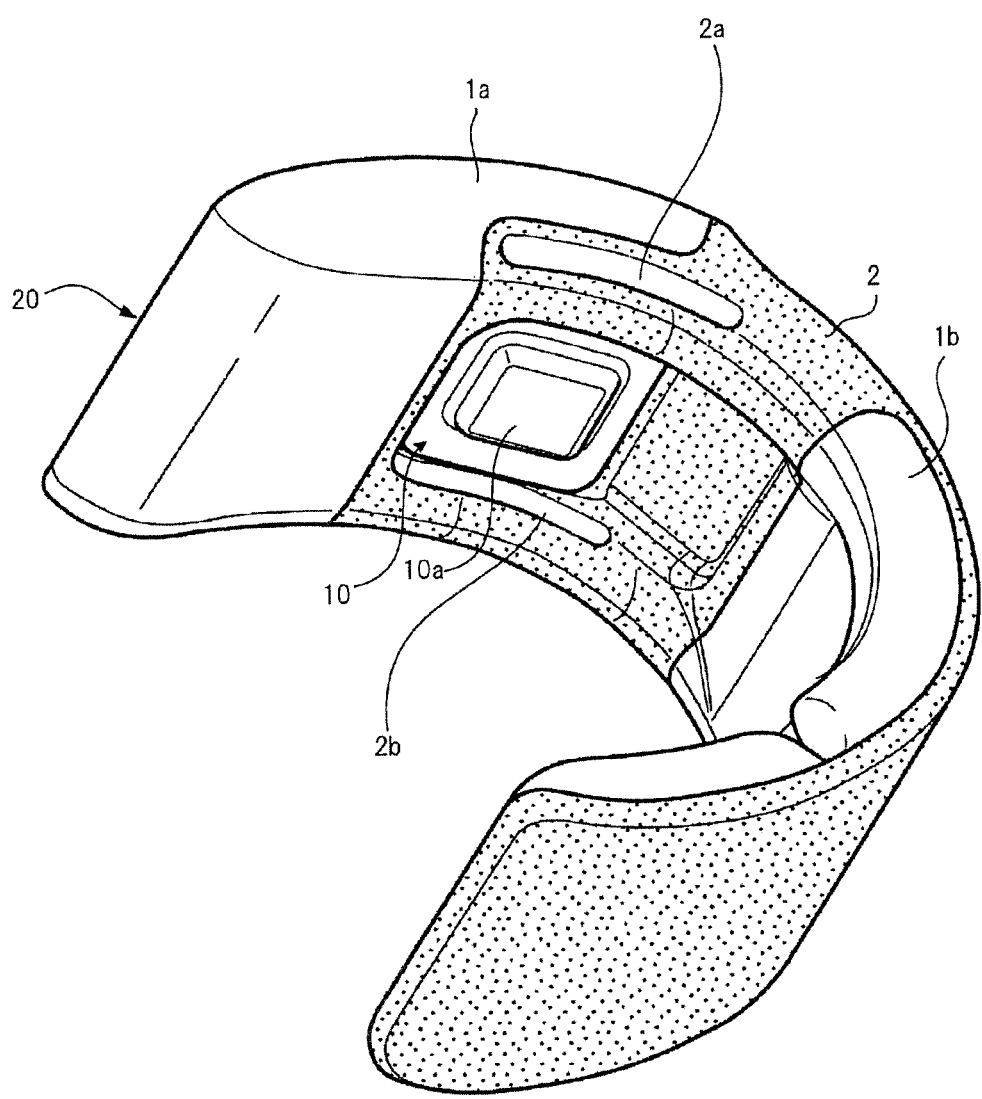
FIG. 2 is a perspective view of the housing 20 shown in FIG. 1, as seen from the side of the inner circumferential surface which is to be in contact with the wrist H.
Figure 3:
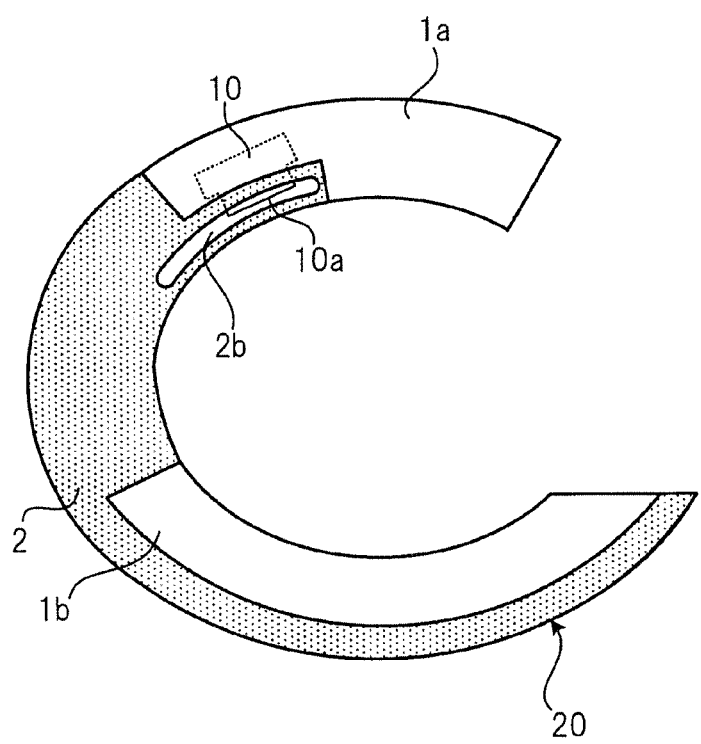
FIG. 3 is a side view of the housing 20 shown in FIG. 1.

FIG. 1 is a diagram showing the external configuration of a biological information measuring device 100 for illustrating an embodiment of the invention. FIG. 2 is a perspective view of the housing 20 shown in FIG. 1, as seen from the side of the inner circumferential surface which is to be in contact with the wrist H. FIG. 3 is a side view of the housing 20 shown in FIG. 1, as seen from the side of the arm of a subject. The biological information measuring device 100 is used while attached to the wrist of the subject.

FIG. 1 shows the left wrist H of the subject. The near side of the figure coincides with the direction in which the hand of the subject exists. The upper side of the figure is in the direction along which the palm of the hand is oriented. In the wrist H, the radius T, the ulna S, and the radial artery TD are shown.

The biological information measuring device 100 has a pressure pulse wave detector 10 which detects a pressure pulse wave from the radial artery TD that extends along the radius T of the wrist H of the subject, and measures biological information such as the blood pressure value and the pulse rate based on pressure pulse waves detected by the pressure pulse wave detector 10.

The pressure pulse wave detector 10 may have a known configuration. For example, the pressure pulse wave detector 10 has a pressure detecting element and a mechanism which presses it against the skin, and detects a pressure pulse wave by using the pressure detecting element.

The biological information measuring device 100 includes the housing 20 which accommodates: the pressure pulse wave detector 10; and a biological information calculator that is not shown, and that calculates biological information such as the blood pressure value and the pulse rate based on the pressure pulse wave detected by the pressure pulse wave detector 10.

The biological information measuring device 100 is requested to have at least the pressure pulse wave detector 10, and functions as the pulse wave detecting device. For example, the biological information calculator may be disposed in an apparatus other than the biological information measuring device 100.

The pressure pulse wave detector 10 has a pressing surface 10a in which one or a plurality of pressure detecting elements are formed (see FIGS. 2 and 3), and the pressing surface 10a can be moved in a direction perpendicular to the pressing surface 10a by the pressing mechanism which is not shown. As shown in FIG. 2, the pressure pulse wave detector 10 is accommodated in the housing 20 in a state where the pressing surface 10a is exposed toward the wrist in the attachment state.

The housing 20 is an approximately U-like housing which is configured so as to be woundable in the peripheral direction (hereinafter, referred to also as the circumferential direction) of the wrist H, and which is opened on the side of the ulna S of the wrist H. The housing 20 has a configuration in which the portion between the both ends in the circumferential direction of the wrist H does not cover the ulna S.

The housing 20 includes: a rigid portion 1 including a rigid portion 1a and a rigid portion 1b; and a flexible portion 2 which is lower in rigidity than the rigid portion 1.

The rigid portion 1a constitutes a tip end part of the housing 20, and has a thickness which is approximately constant in a region extending from the tip end of the housing 20 to a position that is separated from the tip end by a predetermined distance, and which, in the other region that is remoter than the position separated by the predetermined distance, is reduced as progressing from the inner circumferential side of the housing 20 toward the outer circumferential side. A part of the flexible portion 2 overlaps with the portion of the rigid portion 1a where the thickness is reduced.

The flexible portion 2 has a shape which extends from a portion overlapping with the rigid portion 1a, to the rear end of the housing 20. In the portion overlapping with the rigid portion 1a, the thickness of the flexible portion 2 is gradually reduced as progressing from the outer circumferential side of the housing 20 toward the inner circumferential side, and, in the portion of the housing 20 which is to be wound around the back of the hand, the thickness is reduced as progressing from the inner circumferential side of the housing 20 toward the outer circumferential side.

The rigid portion 1b overlaps with the portion of the flexible portion 2 which is on the side of the back of the hand, and in which the thickness is reduced.

Each of the rigid portion 1a and the rigid portion 1b, and the flexible portion 2 are coupled together by fixation such as adhesion or welding, or by coupling pins.

The rigid portion 1a accommodates the pressure pulse wave detector 10. The rigid portion 1a is configured by a first material having a high rigidity in order to stabilize the position of the pressure pulse wave detector 10 with respect to the radial artery TD in the state where the housing 20 is attached to the wrist H, and to protect the pressure pulse wave detector 10 including precision elements. As the first material, for example, a resin or a metal is used.

A part (a portion including the pressing surface 10a) of the pressure pulse wave detector 10 is inserted into a through hole disposed in a portion of the flexible portion 2 which overlaps with the rigid portion 1a, to enter a state where the pressing surface 10a is exposed toward the wrist.

The flexible portion 2 is configured by a second material which is lower in rigidity than the first material. As the second material, for example, an elastic member, a shape-memory alloy, or the like is used.

The rigid portion 1b is configured by the first material in the same manner as the rigid portion 1a, but alternatively may be configured by a material which is different from the first material (preferably, a material which is higher in rigidity than the second material).

In the housing 20, as described above, the portion which is to be wound around a region extending from the side of the palm of the hand to the side of the back of the hand is configured by the flexible portion 2, thereby causing the housing 20 to be easily deformed in accordance with the shape of the wrist H.

As shown in FIG. 1, a band fastener 22 for fixing a band which is not shown, and which is used for securing the housing 20 to the wrist H is disposed on the inner circumferential surface (the surface opposed to the wrist H) of the rigid portion 1b. In the example of FIG. 1, the band fastener 22 is configured by a columnar metal fitting. The basal end of the band is fixed to the band fastener 22.

In the outer circumferential surface (the surface opposite to the surface opposed to the wrist H) of the rigid portion 1a, hole portions II, 12 for engaging the band with the rigid portion 1a are disposed in juxtaposition with each other in the circumferential direction of the wrist H.

The band is configured by a member having a belt-like shape which elongates in the longitudinal direction (synonymous with the circumferential direction of the wrist H) of the housing 20, and which is lower in rigidity than the housing 20. As the member, for example, cloth or leather is used. A hook and loop fastener for affixing band portions together is disposed on the band.

In the biological information measuring device 100, in the state of FIG. 1, the subject causes the tip end portion of the band which is fixed to the band fastener 22, to pass through the hand palm side, inserts the band into the hole portion 12, and then pulls out the band from the hole portion 11.

Thereafter, the subject pulls the band which is taken out from the hole portion 11, to adjust the fastening state, and then causes the band portions to be engaged with each other by the hook and loop fastener, thereby completing the fixing of the housing 20 to the wrist H by the band.

Figure 4:
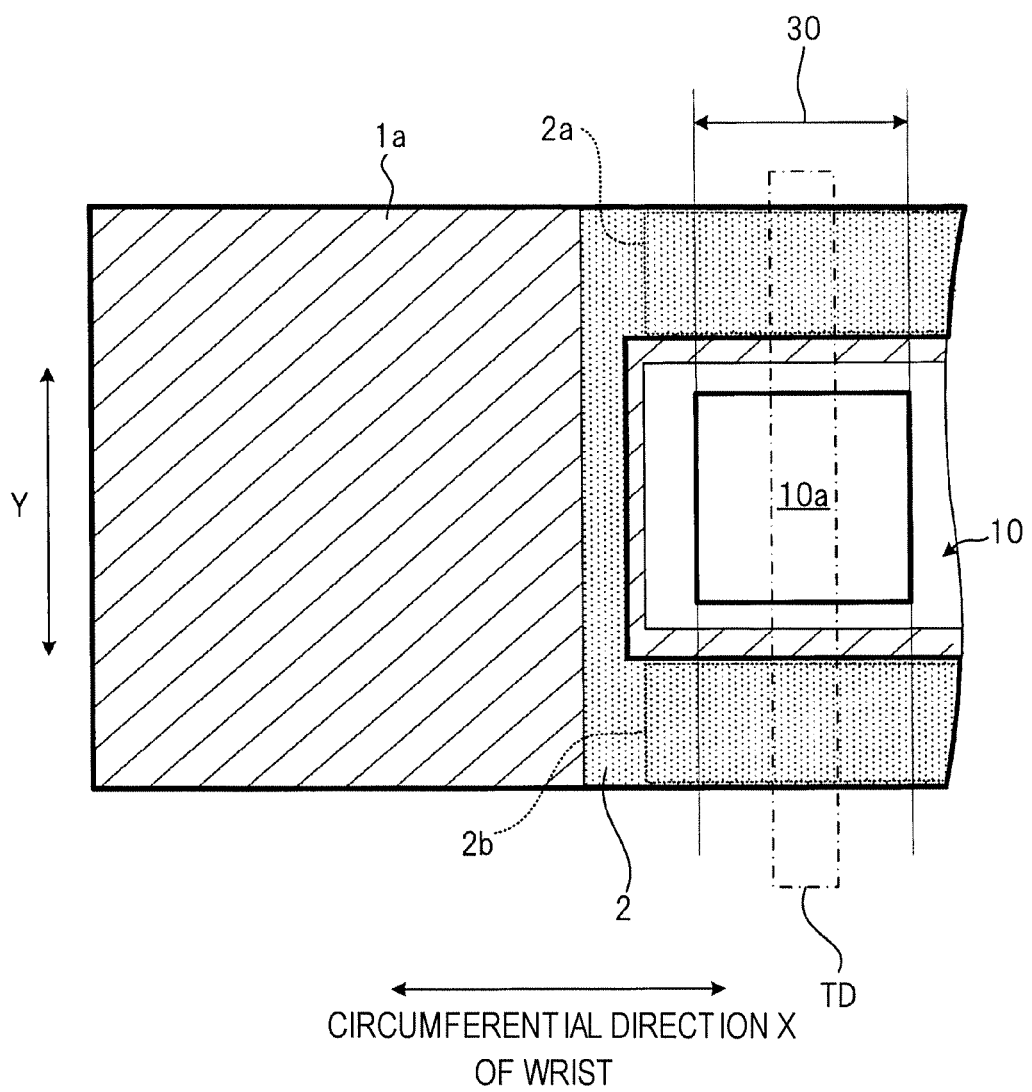
FIG. 4 is a plan view of a part of the housing 20 as seen from the side of the inner circumferential surface which is to be in contact with the wrist.

FIG. 4 is a plan view of a part of the housing 20 as seen in the direction perpendicular to the pressing surface 10a of the pressure pulse wave detector 10 which is accommodated in the housing 20. The portions enclosed by the thick lines shown in FIG. 4 indicate portions which can be contacted with the wrist in a state where the housing 20 is attached to the wrist.

Referring to FIG. 4, cavities 2a, 2b are formed in parts which are in the both end portions of the flexible portion 2 in a direction Y perpendicular to the circumferential direction X of the wrist in the attachment state where the housing 20 is attached to the wrist, and which are adjacent to the pressure pulse wave detector 10.

In the housing 20, the flexible portion 2 which is in the portion (the range indicated by the reference numeral 30 in FIG. 4) overlapping with the pressing surface 10a in the direction Y is contactable with the wrist. The cavities 2a, 2b exist in the portion, and therefore the cavities 2a, 2b enable the portion to be deformed in the direction perpendicular to the pressing surface 10a.

The biological information measuring device 100 is used while the housing 20 is attached to the wrist so as to allow the pressing surface 10a to compress the radial artery TD of the subject. That is, the pressing surface 10a and the radial artery TD always overlap with each other in an attachment state which is recommended by the manufacturer. In the case where the pressing surface 10a and the radial artery TD overlap with each other, also the flexible portion 2 which is in a range indicated by the reference numeral 30 in FIG. 4 overlaps somewhere with the radial artery TD.

In the housing 20, during the attachment state, the flexible portion 2 which is in the range indicated by the reference numeral 30 in FIG. 4, and the pressing surface 10a are in contact with the skin of the subject, and furthermore the pressing surface 10a is pressed toward the radial artery TD. The cavities 2a, 2b exist in the flexible portion 2 in the range. In the attachment state, therefore, the flexible portion 2 is deformed in a manner that the cavities 2a, 2b collapse, and therefore the compression pressure which is exerted by the flexible portion 2 in this range, and which is applied onto the radial artery TD is reduced.

Therefore, the compression pressure which is exerted by the flexible portion 2, and which is applied onto the radial artery TD can be made sufficiently smaller than that which is exerted by the pressing surface 10a, and which is applied onto the radial artery TD. As a result, the radial artery TD is compressed substantially only by the pressing surface 10a, and therefore a pressure pulse wave can be accurately detected.

Although the housing 20 has the cavities 2a, 2b which are longer in the circumferential direction X than the range indicated by the reference numeral 30 in FIG. 4, it is possible to, when a cavity exists at least in this range, attain the effect that the compression pressure which is exerted by the flexible portion 2, and which is applied onto the radial artery TD is reduced. As shown in FIGS. 1 to 4, when the cavities 2a, 2b are formed in a range which is wider than this range, the flexible portion 2 in this range can be deformed more easily, and this is effective.

The rigidity of the flexible portion 2 is not particularly limited as far as the cavities 2a, 2b enable the flexible portion 2 to be deformed. For example, the flexible portion 2 may be configured by the same material as the rigid portion 1a.

Moreover, the housing 20 may have a configuration where the cavities 2a, 2b are filled with a material which is lower in rigidity than the flexible portion 2. Also in this configuration, the flexible portion 2 which is in the range indicated by the reference numeral 30 in FIG. 4 can be deformed in the direction perpendicular to the pressing surface 10a. Therefore, the compression pressure which is exerted by the housing 20, and which is applied onto the radial artery TD can be reduced.

Figure 5:
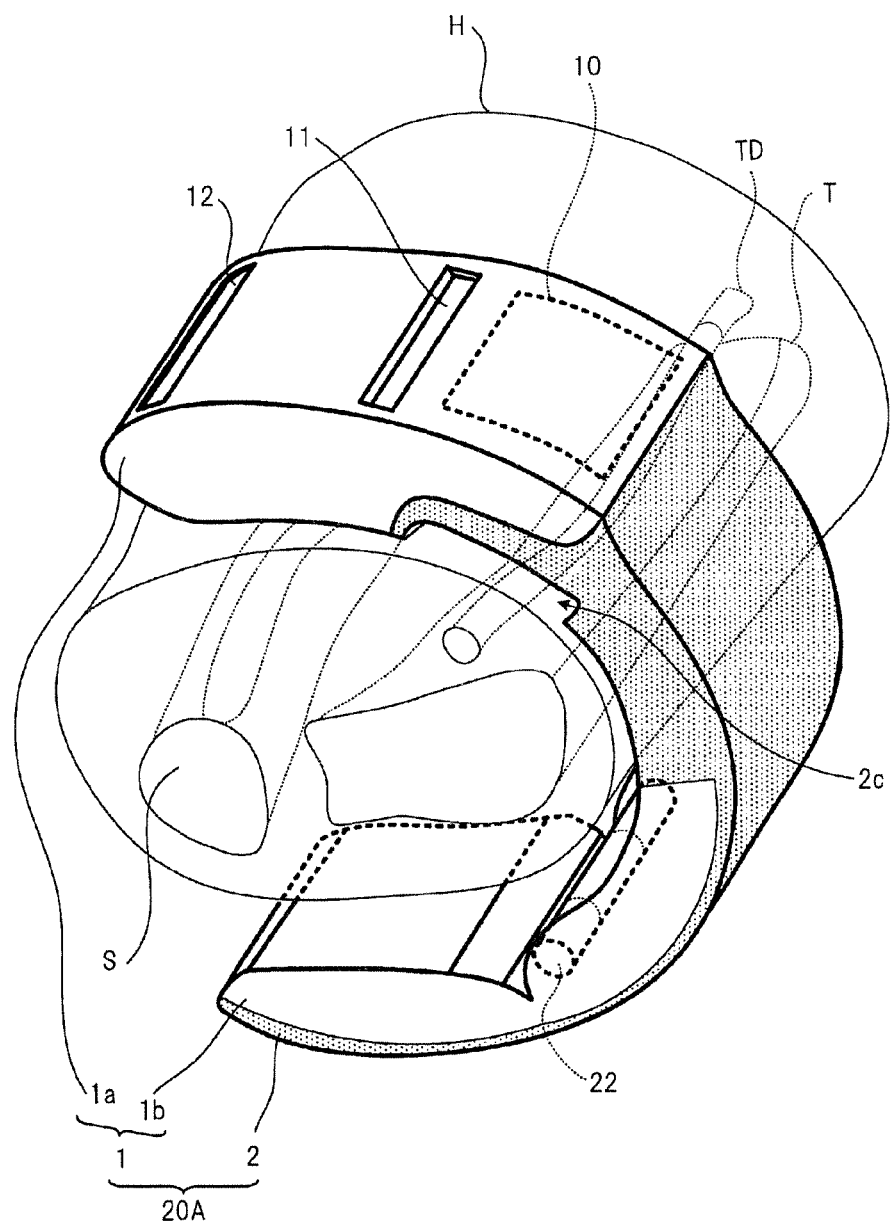
FIG. 5 is a perspective view of a housing 20A which is a modification of the housing 20 of the biological information measuring device 100.
Figure 6:
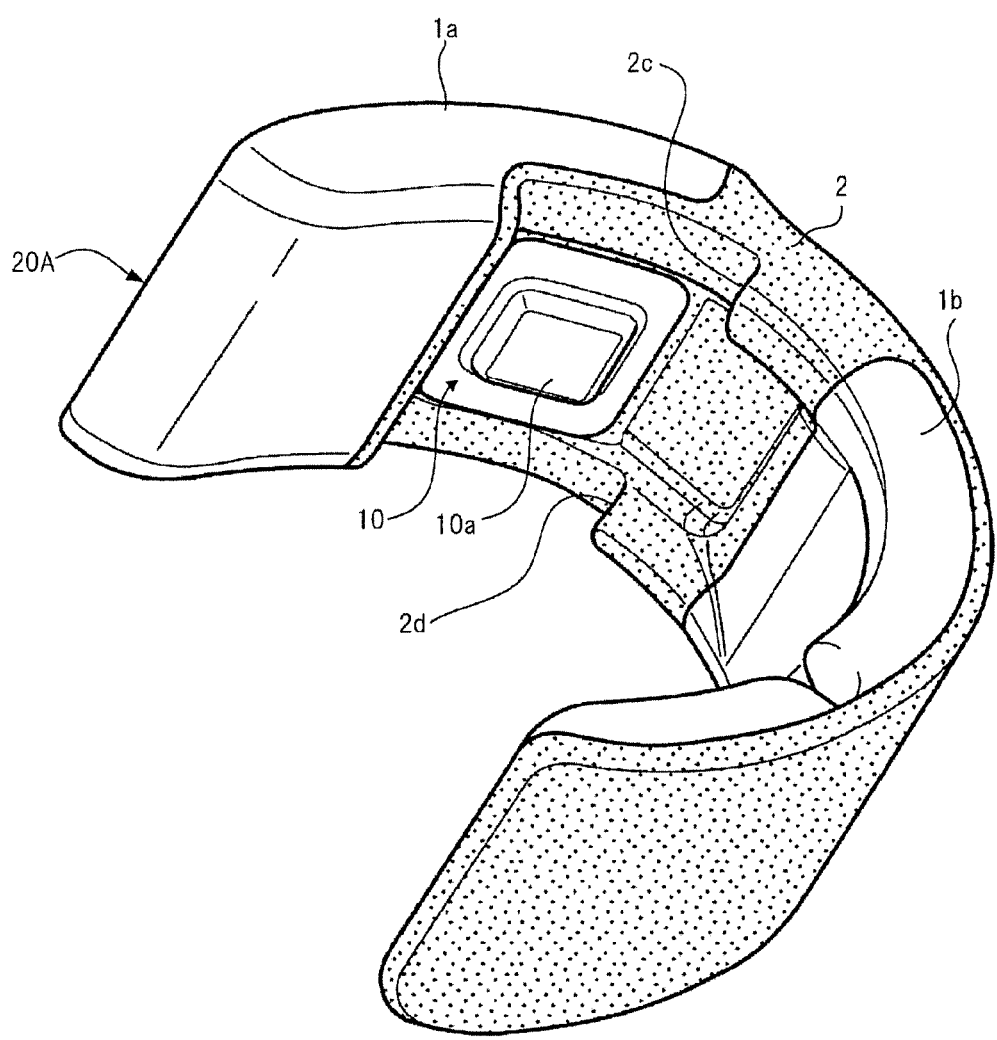
FIG. 6 is a perspective view of the housing 20A as seen from the side of the inner circumferential surface which is to be in contact with the wrist.
Figure 7:
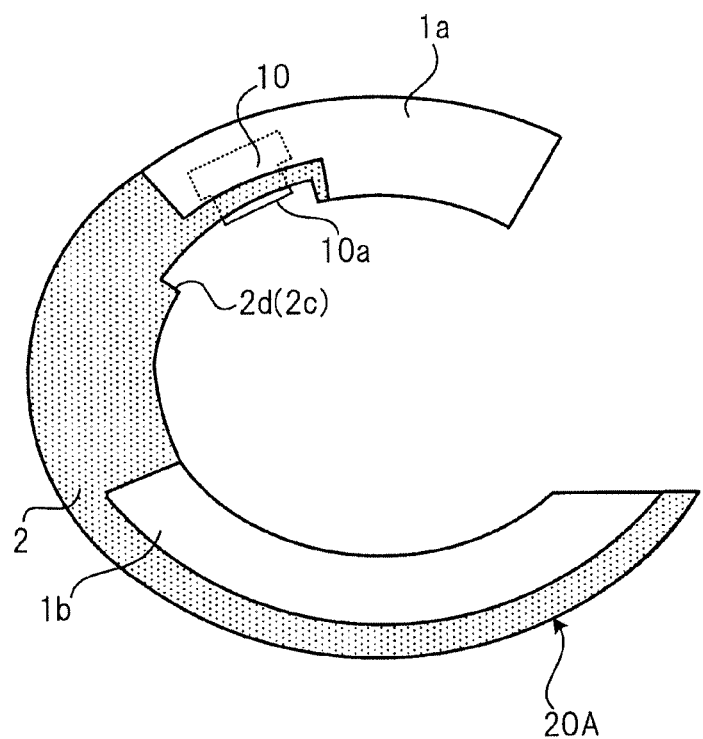
FIG. 7 is a side view of the housing 20A.

FIG. 5 is a perspective view of a housing 20A which is a modification of the housing 20 of the biological information measuring device 100. FIG. 6 is a perspective view of the housing 20A as seen from the side of the inner circumferential surface which is to be in contact with the wrist. FIG. 7 is a side view of the housing 20A as seen from the side of the arm of the subject.

The housing 20A has a configuration in which the portions that are in the flexible portion 2 of the housing 20, and that have the cavities 2a, 2b are changed to recesses 2c, 2d.

Figure 8:
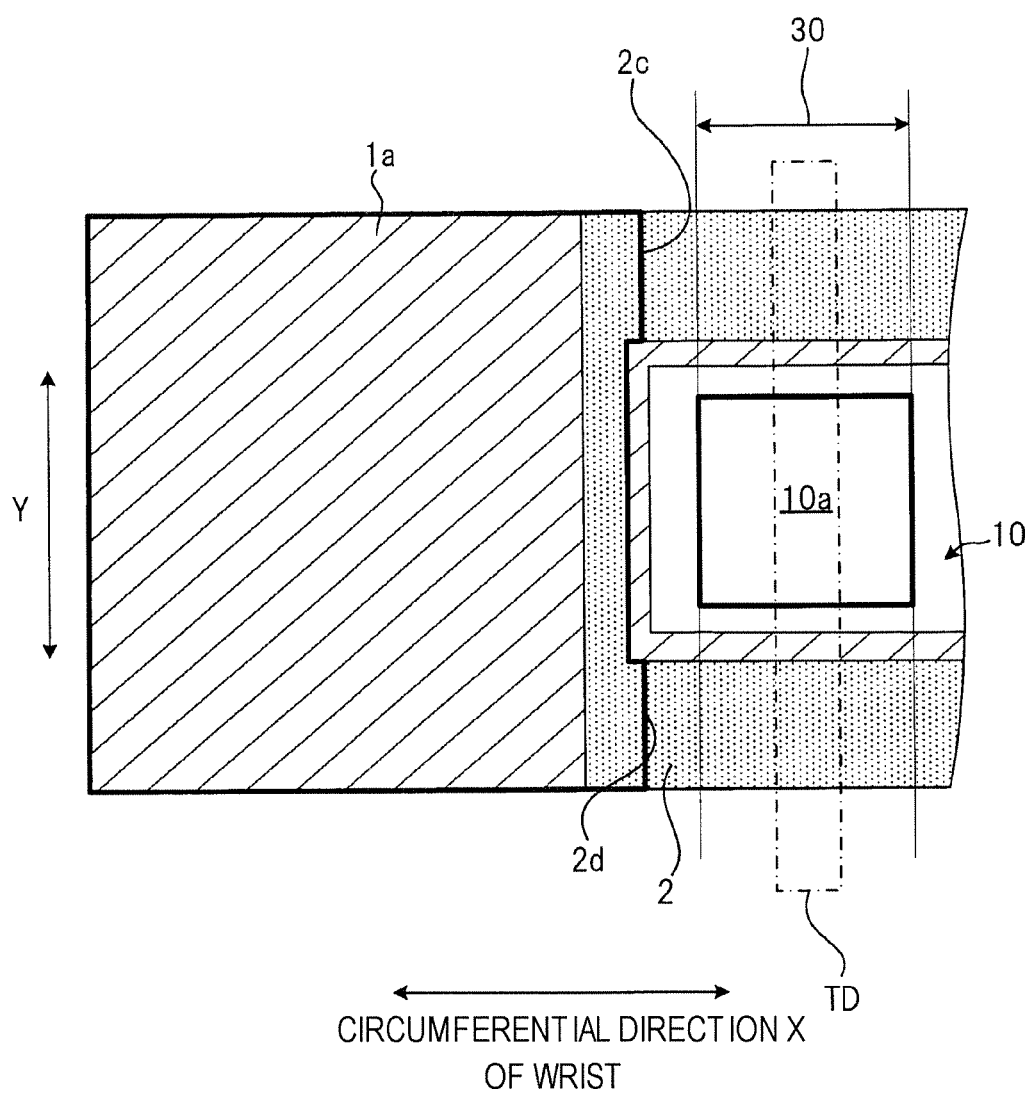
FIG. 8 is a plan view of a part of the housing 20A as seen from the side of the inner circumferential surface which is to be in contact with the wrist.

FIG. 8 is a plan view of a part of the housing 20A as seen in the direction perpendicular to the pressing surface 10a of the pressure pulse wave detector 10 which is accommodated in the housing 20. The portions enclosed by the thick lines shown in FIG. 8 indicate portions which can be contacted with the wrist in a state where the housing 20A is attached to the wrist.

Referring to FIG. 8, the recesses 2c, 2d are formed in the inner circumferential surfaces of parts which are in the both end portions of the flexible portion 2 in the direction Y perpendicular to the circumferential direction X of the wrist in the attachment state, and which are adjacent to the pressure pulse wave detector 10.

In the housing 20A, as described above, the portion (the range indicated by the reference numeral 30 in FIG. 8) overlapping in the direction Y with the pressing surface 10a is at a position where the portion cannot be contacted with the wrist in the attachment state (a position which is closer to the outer circumferential surface of the housing 20A than the pressing surface 10a in the direction perpendicular to the pressing surface 10a).

In the attachment state, therefore, the radial artery TD of the subject is compressed only by the pressing surface 10a. Consequently, the compression pressure which is exerted by the housing 20A, and which is applied onto the radial artery TD can be made sufficiently smaller than that which is exerted by the pressing surface 10a, and which is applied onto the radial artery TD, and therefore a pressure pulse wave can be accurately detected.

Although the housing 20A has the recesses 2c, 2d which are larger in the circumferential direction X than the range indicated by the reference numeral 30 in FIG. 8, it is possible to, when a recess exists at least in this range, attain the effect that the compression pressure which is exerted by the housing 20A, and which is applied onto the radial artery TD is reduced.

The presently disclosed embodiment should be considered in all respects to be illustrative and not restrictive. The scope of the invention is indicated by the appended claims rather than the foregoing description, and all changes which come within the meaning and range of equivalents thereof are intended to be embraced therein.

As described above, the following matters are disclosed in the specification.

The disclosed pulse wave detecting device includes: a pressure pulse wave detector which is configured to press a pressing surface in which a pressure detecting element is formed, against a radial artery under a skin of a wrist of a subject, and which is configured to detect a pressure pulse wave from the radial artery; and a housing which accommodates the pressure pulse wave detector in an attachment state where the pressing surface is exposed toward the wrist, and the housing is configured so that a compression pressure which is exerted by the housing in an attachment state where the housing is attached to the wrist, and which is applied onto the radial artery is smaller than a compression pressure which is exerted by the pressing surface in the attachment state, and which is applied onto the radial artery.

In the disclosed vital pulse wave detecting device, a portion of the housing which, in a plan view of the pressing surface, overlaps with the pressing surface in a direction perpendicular to a circumferential direction of the wrist in the attachment state is at a position where the portion is not contactable with the wrist in the attachment state.

In the disclosed vital pulse wave detecting device, a portion of the housing which, in a plan view of the pressing surface, overlaps with the pressing surface in a direction perpendicular to a circumferential direction of the wrist in the attachment state includes a part which is contactable with the wrist in the attachment state, and the part which is contactable with the wrist is deformable in a direction perpendicular to the pressing surface.

In the disclosed vital pulse wave detecting device, the part which is contactable with the wrist internally includes a cavity, and the cavity enables the part to be deformed in the direction perpendicular to the pressing surface.

According to the invention, it is possible to provide a pulse wave detecting device in which the accuracy of detection of a pressure pulse wave can be improved.

Although the invention has been described with reference to the specific embodiment, the invention is not limited to the embodiment, and various changes can be made without departing from the technical spirit of the disclosed invention.

What is claimed is:

1. A pulse wave detecting device comprising:
  a pressure pulse wave detector which is configured to press a pressing surface in which a pressure detecting element is formed, against a skin above a radial artery in a wrist of a subject, and which is configured to detect a pressure pulse wave from the radial artery;
  a housing which comprises a first rigid portion and a second rigid portion, and a flexible portion which is lower in rigidity than the first rigid portion and the second rigid portion, and which accommodates the pressure pulse wave detector with the first rigid portion in a state where the pressing surface is exposed toward the wrist by inserting the pressing surface into a through hole disposed in a portion of the flexible portion which overlaps with the first rigid portion,
  wherein the portion of the flexible portion overlaps with a portion of the first rigid portion where a thickness from an inner circumferential side of the first rigid portion toward an outer circumferential side of the first rigid portion is reduced in comparison of a thickness of the flexible portion,
  wherein in an attachment state where the housing is attached to the wrist, the flexible portion which, at a position adjacent to the pressing surface, is contacted with the skin above the radial artery together with the pressing surface, is deformable in a direction perpendicular to the pressing surface,
  wherein a compression pressure which is exerted by the flexible portion in the attachment state, and which is applied onto the radial artery is smaller than a compression pressure which is exerted by the pressing surface, and which is applied onto the radial artery,
  wherein the flexible portion internally includes a hole, and the hole enables the flexible portion to be deformed in the direction perpendicular to the pressing surface, and
  wherein the hole is through and extends from the portion of the flexible portion which overlaps with the portion of the first rigid portion where the thickness is reduced, beyond the portion of the flexible portion and into the first rigid portion.

2. The pulse wave detecting device according to claim 1, wherein the housing is U-shaped and is open on a side of ulna of the wrist.

* * * * *